United States Patent

Jacobs

Patent Number: 5,511,555
Date of Patent: Apr. 30, 1996

[54] NEUROLOGICAL PIN

[76] Inventor: Barry L. Jacobs, 52 Crespigny Road, London N.W.4 3DX, England

[21] Appl. No.: 318,751
[22] PCT Filed: Mar. 3, 1993
[86] PCT No.: PCT/GB93/00431
§ 371 Date: Sep. 12, 1994
§ 102(e) Date: Sep. 12, 1994
[87] PCT Pub. No.: WO93/17617
PCT Pub. Date: Sep. 16, 1993

[30] Foreign Application Priority Data

Mar. 10, 1992 [GB] United Kingdom ............ 9205324
Oct. 23, 1992 [GB] United Kingdom ............ 9222276

[51] Int. Cl.$^6$ ............................................. A61B 19/00
[52] U.S. Cl. ............................................. 128/744
[58] Field of Search ................................. 128/739, 740, 128/744; 607/167

[56] References Cited

U.S. PATENT DOCUMENTS 2,532,093  11/1950  Golub et al. ................ 128/744
3,185,146   5/1965  Leopoldi ..................... 128/744
3,662,744   5/1972  Low et al. ................... 128/744
3,933,148   1/1976  Wyler et al. ................. 128/744
4,964,412  10/1990  Kelly ......................... 128/744

FOREIGN PATENT DOCUMENTS 2709340  9/1977  Germany ..................... 128/740

Primary Examiner—Max Hindenburg
Attorney, Agent, or Firm—Suzanne F. Seavello; Hopkins & Carley

[57] ABSTRACT

A neurological pin includes a shaft with a sharp end and a blunt end. The sharp end is surrounded by an element defining an annular surface traversing the axis of the shaft. The blunt end is normally defined by a spherical body and typically, the diameter of the sphere will be substantially equal to that of the annular surface. The element defining the annular surface is frustro-conical, tapering towards the blunt end. The provision of the annular surface at the sharp end of the shaft substantially eliminates the risk of piercing a patient's skin during normal use, while facilitating the application of consistent pressure on the skin.

17 Claims, 2 Drawing Sheets

NEUROLOGICAL PIN

This invention relates to neurological pins. They are used for testing objective sensation; for example, awareness of the difference between sharp (pain) and blunt by comparison between a sharp point and a rounded end on the patient's skin. These are provided at opposite ends of the pin.

The most commonly used neurological pin consists of a relatively narrow rod, of which one end is sharpened to provide the point, and the other end carries a spherical body for providing the rounded end for blunt sensation. It is used by grasping it between thumb and forefinger, pincer like, halfway between its two ends and applying one or the other to the patient's, asking the patient, whose eyes are closed or at least is not watching, to identify which end is being used. The clinician's hand has to invert or switch the pin through 180° to change ends. Pressure, is applied manually and may vary. Although not as sharp as a needle, the sharp end of the pin is still easily capable of penetrating skin, especially in the hands of the inexperienced, the fatigued or the over zealous.

The traditional neurological pin has been looked upon as a permanent piece of equipment, traditionally to be found in the lapel of the hospital doctor's coat and the consultant's jacket or in the family doctor's bag. It would be used from patient to patient as the hospital practitioner moves form bed to bed, or as the GP moves from house to house. The pin is placed back in its place of storage with as much afterthought as the stethoscope. It may be used by the practitioner on multiple occasions in one day. There are obvious risks involved in such multiple utilisation of the same piece of equipment. The multiple use of an item which can potentially puncture the skin involves a particular risk of cross-infection.

The present invention is directed at a neurological pin, broadly of the traditional type as described above, but adapted to minimise the risk of the patients' skin being puncture during its use. According to the invention, a neurological pin comprises a shaft with a sharp end and a blunt end wherein the sharp end is surrounded by an element defining an annular surface traversing the axis of the shaft. The element defining the annular surface is frusto-conical, tapering toward the blunt end. The blunt end is normally defined by a spherical body and typically, the diameter of the sphere will be substantially equal to that of the annular surface.

In preferred embodiments of the invention the annular surface defines a plane from which the sharp end of the shaft projects. Normally, the annular surface is substantially circular, and the sharp end projects beyond the plane of the annulus by a distance not exceeding the radius thereof. The element may have a substantially planar surface defined by the annular surface and normally perpendicular to the shaft, from which the sharp end of the shaft projects. While these arrangements are currently preferred, the disposition of the sharp end or point relative to the annular surface can be varied. For example the point at the sharp end of the shaft may reach to and lay within the plane of the annular surface. In another example, the point at the sharp end of the shaft may not reach to the plane of the annular surface, but lay within the element.

The element defining the annular surface at the sharp end of the pin shaft is usually substantially rigid, and normally fixed to the shaft. It may be formed integrally therewith.

The sharp end of the pin shaft will define a point at its tip. The actual shape of this point can be significant. I have found that better; i.e., better assessable responses, can be achieved if the actual tip is flattened. The area of the flattened tip will be small, normally in the range $6.2 \times 10^{-4}$ mm$^2$ to 0.04 mm$^2$. A typical area is 0.025 mm$^2$. The shape of the tip area may vary, but is preferably substantially square.

Neurological pins of the invention offer a number of benefits. They may be made of plastics material in a moulding process. They can be sterilised at the point of manufacture or of packaging, and may be kept so sterilised up to the up to the point of use. They can be inexpensive to manufacture, and therefore made disposable. Handling and use can be facilitated by the enlargements normally present at both ends, and further assisted by the provision of a friction area midway down the shaft. Most significantly perhaps, the provision of the annular surface at the sharp end of the shaft can substantially eliminate the risk of piercing a patient's skin during normal use, while facilitating the application of consistent pressure on the skin during use.

The invention will now be described by way of example and with reference to the accompanying drawings wherein.

Figure 1:
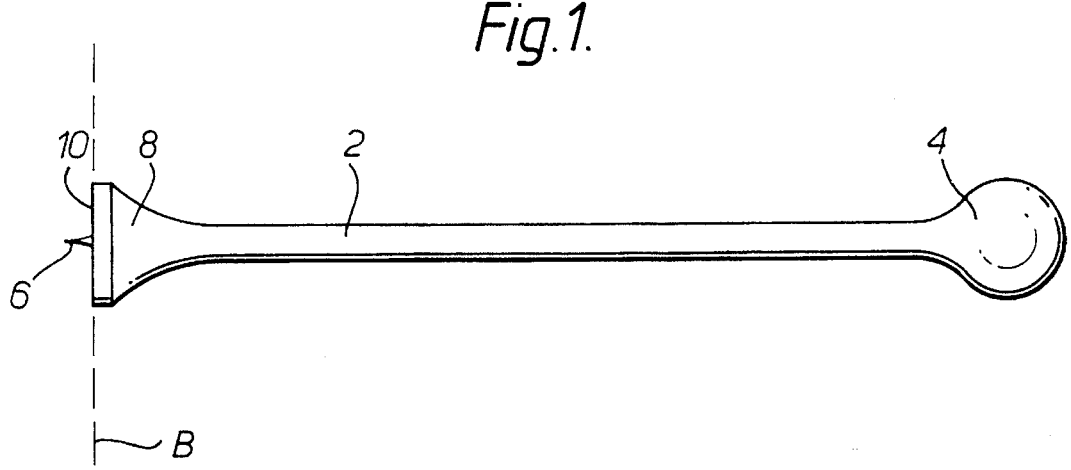
FIGS. 1 and 2 are side views of two embodiments of the invention.

The neurological pin 1 shown in FIG. 1 comprises a shaft 2 at one end of which is formed a solid sphere 4, and at the other end is formed a point 6 which projects from an enlarged section 8. The Pin 1 can be moulded in a suitable plastics material such as polythene or ABS, and is typically around 6 cms long. The Enlarged substantially conical section 8 defines an annular surface 10, better shown in FIGS. 3 and 4, in a plane B which traverses the axis of the shaft 2. The diameter of the annular surface 10 is substantially equal to that of the sphere 4 at around 5 mms.

Figure 2:
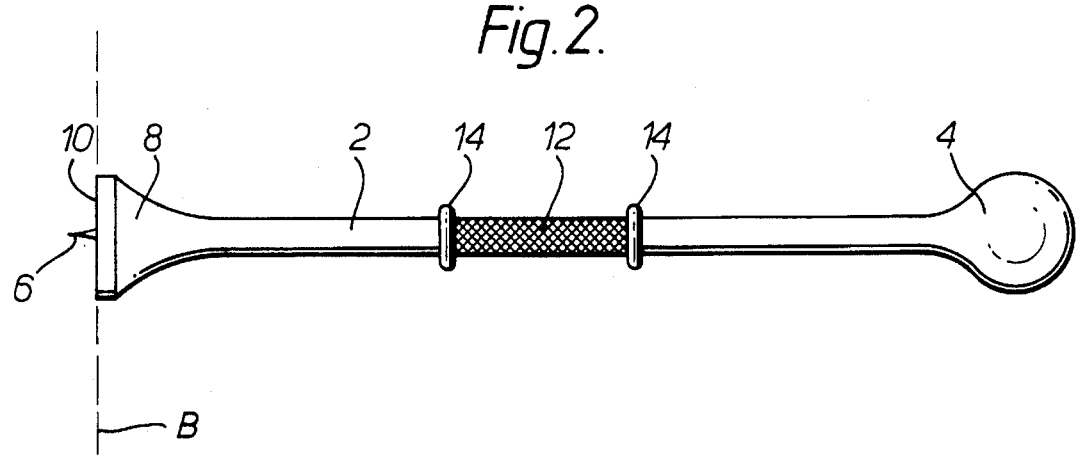

Pin 1 shown in FIG. 2 differs from that of FIG. 1 in that a central position 12 of shaft 2 is formed with a knurled or roughened section bounded by two annular projections 14. This section can make it easier to hold the pin 1, inhibit or control slippage, and facilitate pivoting or inverting pin 1 in use to apply alternate ends to a patient's skin.

Figure 3:
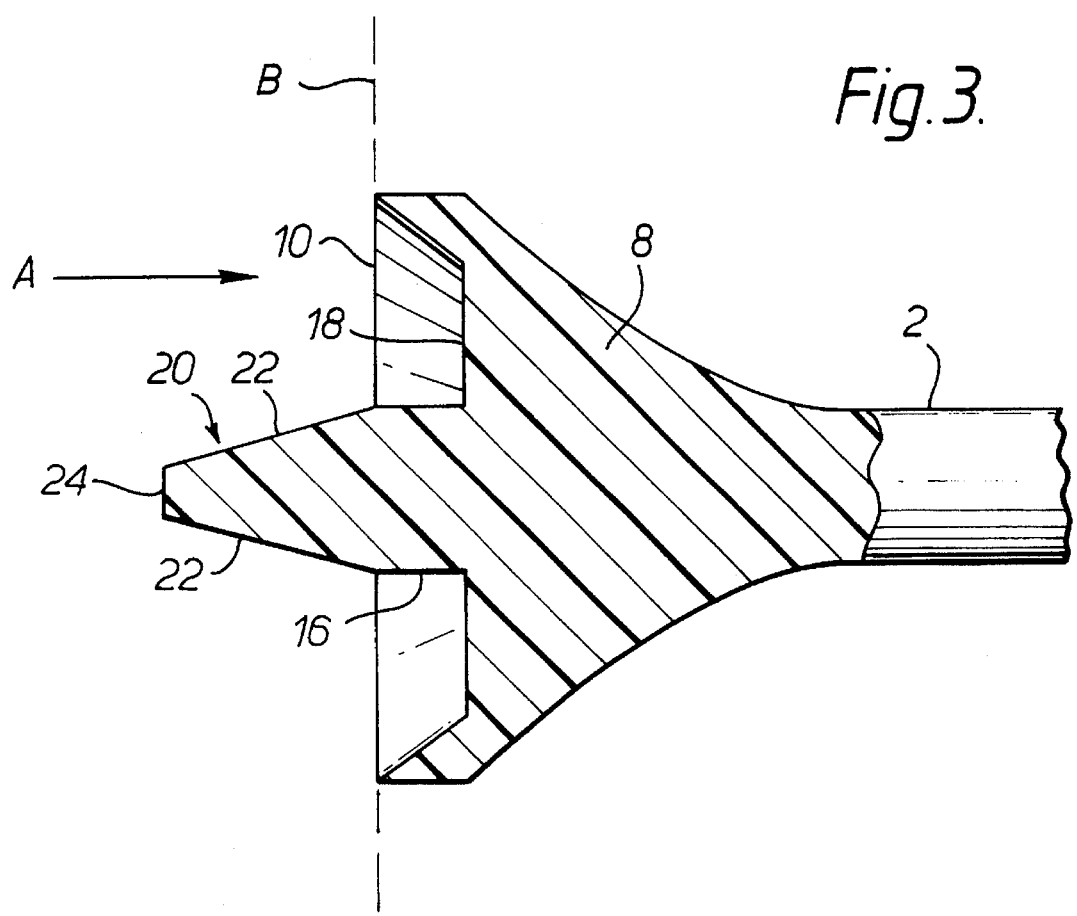
FIG. 3 is an enlarged detail side view of the sharp end of the pin shown in FIG. 1 or in FIG. 2 showing the point thereat.
Figure 4:
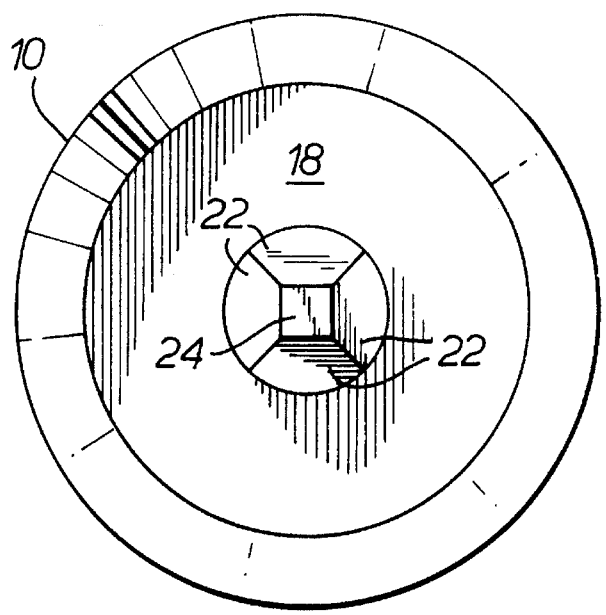
FIG. 4 is a view taken in the direct of arrow A in FIG. 3.

In the detail views of FIGS. 3 and 4, the shape and configuration of point 6 is clearly shown projecting from the plane defined by the annular surface 10. The surface 10 actually extends around a recess formed in the section 8, and the base 16 of the point 6 protrudes from the floor 18 of the recess. This base 16 is of uniform circular cross-section up to the plane defined by the annular surface 10. The upper section 20 of the point has been machined to form four planar sides 22 which converge towards a flat surface 24 at the distal extremity. The shape of the flat surface is thus square, with an area typically up to 0.025 mm$^2$. The configuration of point 6 at-the sharp end of shaft 2 is not critical, but a flat surface of the type illustrated is preferred as it has been found to provoke a particularly effective and assessable response from a patient when applied to the skin.

The enlarged section 8 serves the effective function of restricting the depth to which the point 6 can press into a patient's skin. While the formation of the recess is sometimes preferred, in modification of the configuration shown in FIGS. 3 and 4 the recess is filled, and the surface 10 is not strictly annular, but circular.

While the point 6 of the pin shown in the drawings projects from the plane defined by the annular surface 10, in some embodiments of the invention, the distal extremity can be located in the plane, or even on the other side thereof; i.e., within the recess, if more sensitive responses are under review.

The enlarged section of shaft 2 is shown as an integral part of the shape. However, it may be a separate element, and in some case it can be mounted for axial movement along shaft 2 to alter the extent to which the distal extremity of point 6 projects or fails to project from the plane of the annular surface.

In most cases, the enlarged section will be substantially rigid, but a degree of flexibility can be desirable in some circumstances. Nevertheless, it is important that the basic function of the annular surface, to provide some protection for, and define a plane relative to point 6, is preserved.

Neurological pins according to the invention can be easily and economically manufactured and packaged, and can be sterilised for single patient use and subsequent disposal. They are thus particularly beneficial in terms of hygiene and cleanliness. The enlarged section and the annular surface thereon ensures that consistent and accurate tests can be performed, with minimal risk of skin penetration. It also reduces the chance of a practitioner injuring himself or herself accidentally, as the full effect of the sharp end of the shaft 2, which is itself restricted by the annular surface, is only available when shaft 2 is substantially perpendicular to the skin.

I claim:

1. A neurological pin comprising a shaft with a sharp end and a blunt end, both for testing objective sensation, wherein the sharp end is surrounded by an element defining an annular surface traversing the axis of the shaft, which element is fixed relative to the shaft and determines the extent to which the sharp end can impress the skin of a patient under a given force.

2. A neurological pin according to claim 1 wherein the annular surface defines a plane substantially containing the point at the sharp end of the shaft.

3. A neurological pin according to claim 1 wherein the annular surface defines a plane from which the sharp end of the shaft projects.

4. A neurological pin according to claim 3 wherein the annular surface is substantially circular, and the sharp end projects beyond the plane of the annulus by a distance not exceeding the radius thereof.

5. A pin according to claim 3 or claim 4 wherein the annular surface is the boundary of a substantially planar surface perpendicular to the shaft and from which the sharp end of the shaft projects.

6. A neurological pin according to claim 1 wherein the annular surface defines a plane traversing the axis of the shaft beyond the sharp end thereof.

7. A neurological pin according to claim 1 wherein the surrounding element is substantially rigid.

8. A neurological pin according to claim 1 wherein the surrounding element is fixed to the shaft.

9. A neurological pin according to claim 1 wherein the surrounding element is substantially conical, and convergent towards the blunt end of the shaft.

10. A neurological pin according to claim 1 including a toughened region formed on the shaft.

11. A neurological pin according to claim 1 wherein the shaft is formed with a lateral projection.

12. A neurological pin according to claim 1 wherein the blunt end of the shaft comprises a spherical body.

13. A neurological pin according to claim 1 wherein the tip at the sharp end of the shaft defines a substantially flat surface traversing the shaft axis.

14. A neurological pin according to claim 13 wherein the shape of the flat surface is square.

15. A neurological pin according to claim 1 moulded in a plastics material.

16. A neurological pin comprising a shaft with a sharp end and a blunt end, both for testing objective sensation, wherein the sharp end is surrounded by an element defining an annular surface traversing the axis of the shaft which element is formed integral with the shaft and determines the extent to which the sharp end can impress the skin of a patient under a given force.

17. A neurological pin moulded in a plastics material and comprising a shaft sharp at one end and having a sphere at the other end, with a conical element fixed on the shaft adjacent the sharp end, the element being disposed symmetrically on the shaft and tapering towards said other end and thereof whereby the base of the conical element defines an annular surface traversing the axis of the shaft, the base determining the extent to which the sharp end can impress the skin of a patient under a given force.

* * * * *